United States Patent
Conroy et al.

(10) Patent No.: US 11,126,921 B2
(45) Date of Patent: Sep. 21, 2021

(54) LEARNING AND APPLYING CONTEXTUAL SIMILARITIES BETWEEN ENTITIES

(71) Applicant: KONINKLIJKE PHILIPS N.V., Eindhoven (NL)

(72) Inventors: Bryan Conroy, Garden City South, NY (US); Minnan Xu, Cambridge, MA (US); Asif Rahman, Brookline, MA (US); Cristhian Mauricio Potes Blandon, Salem, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 750 days.

(21) Appl. No.: 15/957,232

(22) Filed: Apr. 19, 2018

(65) Prior Publication Data

US 2018/0307995 A1 Oct. 25, 2018

Related U.S. Application Data

(60) Provisional application No. 62/608,878, filed on Dec. 21, 2017, provisional application No. 62/487,720, filed on Apr. 20, 2017.

(51) Int. Cl.
*G06N 5/04* (2006.01)
*G06N 20/00* (2019.01)
(Continued)

(52) U.S. Cl.
CPC ............ *G06N 5/048* (2013.01); *G06N 5/022* (2013.01); *G06N 20/00* (2019.01); *G06N 20/10* (2019.01);
(Continued)

(58) Field of Classification Search
CPC ........ G06N 5/048; G06N 5/022; G06N 20/00; G06N 20/10; G06N 99/005; G16H 50/30; G16H 50/20; G16H 50/70; G16H 40/63
(Continued)

(56) References Cited

U.S. PATENT DOCUMENTS

| 7,899,764 B2 | 3/2011 | Martin et al. |
| 2008/0201280 A1* | 8/2008 | Martin .................... G06F 19/00 706/12 |

(Continued)

FOREIGN PATENT DOCUMENTS

| WO | 2012080906 A1 | 6/2012 |
| WO | 2016100638 A1 | 6/2016 |

OTHER PUBLICATIONS

Chan et al., "Machine Learning of Patient Similarity", 2010 IEEE International Conference on Bioinformatics and Biomedicine Workshops. (Year: 2010).*

(Continued)

*Primary Examiner* — Dave Misir

(57) ABSTRACT

Techniques disclosed herein relate to learning and applying contextual patient similarities. Multiple template similarity functions may be provided. Each template similarity function may compare a respective subset of features of a query entity feature vector with a corresponding subset of features of a candidate entity feature vector. A composite similarity function may be provided as a weighted combination of respective outputs of the template similarity functions. A plurality of labeled entity vectors may be provided as context training data. An approximation function may be applied to approximate a first context label for each respective labeled entity vector. A first context specific composite similarity function may be trained based on the composite similarity function by learning first context weights for the template similarity functions using a first loss function based on output of application of the approximation function to the first context training data.

20 Claims, 8 Drawing Sheets

(51) Int. Cl.

| | |
|---|---|
| *G16H 50/30* | (2018.01) |
| *G16H 20/17* | (2018.01) |
| *G06N 20/10* | (2019.01) |
| *G06N 5/02* | (2006.01) |
| *G16H 40/63* | (2018.01) |
| *G16H 50/70* | (2018.01) |
| *G16H 50/20* | (2018.01) |

(52) U.S. Cl.
CPC ............. *G16H 20/17* (2018.01); *G16H 40/63* (2018.01); *G16H 50/20* (2018.01); *G16H 50/30* (2018.01); *G16H 50/70* (2018.01)

(58) Field of Classification Search
USPC .......................................................... 706/12
See application file for complete search history.

(56) References Cited

U.S. PATENT DOCUMENTS

| | | | | |
|---|---|---|---|---|
| 2012/0089551 | A1* | 4/2012 | Ebadollahi | G06N 5/047 706/48 |
| 2013/0268547 | A1* | 10/2013 | Boroczky | G16H 50/70 707/758 |
| 2013/0310653 | A1* | 11/2013 | Zillner | G06N 5/00 600/300 |
| 2014/0003697 | A1* | 1/2014 | Qian | G06T 7/0014 382/131 |
| 2014/0279729 | A1* | 9/2014 | Delaney | G06N 5/02 706/12 |
| 2014/0344208 | A1* | 11/2014 | Ghasemzadeh | G06F 19/00 706/52 |
| 2016/0103973 | A1* | 4/2016 | Singal | G16H 70/60 705/3 |
| 2016/0148116 | A1* | 5/2016 | Bornea | G06N 5/022 706/12 |
| 2017/0083682 | A1* | 3/2017 | McNutt | A61N 5/1031 |
| 2018/0032678 | A1* | 2/2018 | Dandala | G06F 19/00 |
| 2018/0098737 | A1* | 4/2018 | Villazon-Terrazas | A61B 5/0022 |
| 2020/0327404 | A1* | 10/2020 | Miotto | G06N 3/0454 |

OTHER PUBLICATIONS

Zhan et al., "Low-Rank Sparse Feature Selection for Patient Similarity Learning", 2016 IEEE 16th International Conference on Data Mining. (Year: 2016).*

Zhu et al., "Measuring Patient Similarities via A Deep Architecture with Medical Concept Embedding", 2016 IEEE 16th International Conference on Data Mining. (Year: 2016).*

Sun et al., "Supervised Patient Similarity Measure of Heterogeneous Patient Records", SIGKDD Explorations, 2012. (Year: 2012).*

Sharafoddini, A. et al., "Patient Similarity in Prediction Models Based on Health Data: A Scoping Review", JMIR Medical Informatics, vol. 5, issue 1, 2017.

Gönen, M. et al., "Multiple Kernel Learning Algorithms", Journal of Machine Learning Research, 2009.

Longhurst, C. et al., "The green button idea", Stanford University, 2015, http://shahlab.stanford.edu/greenbutton.

"Clinical Looking Glass", Montefiore Medical Center, http://exploreclg.montefiore.org/world-of-clg.aspx, Accessed Jan. 2019.

Gotz, D. et al., "Visual cluster analysis in support of clinical decision intelligence", Oct. 2011.

Ahmed M.U., et al., "Case-Based Reasoning for Medical and Industrial Decision Support Systems", In: Montani S., Jain L.C. (eds) Successful Case-based Reasoning Applications—I. Studies in Computational Intelligence, vol. 305. Springer, Berlin, Heidelberg, 2010.

* cited by examiner

Fig. 3

PATIENT DASHBOARD: JOHN DOE                                     300

CARDIOVASCULAR  330₁
HEART RATE: _____
NIBP MEAN: _____
NITROGLYCERIN: _____

CRS  330₂
HEMOGLOBIN: _____
IONIZED CALCIUM: _____
LACTATE: _____

CDS STATS  330₅
HII: 78***
LACTATE: _____
MAGNESIUM: _____
PEAK...: _____
POTASSIUM: _____
PTT: _____
ARTERIAL PaCO2: _____
ACUTE KIDNEY INJURY
ARDS

RENAL  330₃
URINE OUTPUT: _____
FLUID BALANCE: _____
SODIUM CHLORIDE: _____

RESPIRATORY  330₄
RESP. RATE: _____
SpO2: _____
COUGH: _____

700

```
┌─────────────────────────────────────────────────────────────────────┐
│ DISPLAY, ON AN INTERFACE, A FIRST VALUE FOR A QUERY ENTITY, WHEREIN │
│         THE FIRST VALUE IS RELATED TO A FIRST CONTEXT               │
│                              702                                    │
└─────────────────────────────────────────────────────────────────────┘
                                  ↓
┌─────────────────────────────────────────────────────────────────────┐
│ SELECT A FIRST TRAINED SIMILARITY FUNCTION FROM A PLURALITY OF      │
│ TRAINED SIMILARITY FUNCTIONS, WHEREIN THE FIRST TRAINED SIMILARITY  │
│          FUNCTION IS ASSOCIATED WITH THE FIRST CONTEXT              │
│                              704                                    │
└─────────────────────────────────────────────────────────────────────┘
                                  ↓
┌─────────────────────────────────────────────────────────────────────┐
│ APPLY THE FIRST SELECTED TRAINED SIMILARITY FUNCTION TO A SET OF    │
│ FEATURES ASSOCIATED WITH THE QUERY ENTITY AND RESPECTIVE SETS OF    │
│         FEATURES ASSOCIATED WITH A PLURALITY OF CANDIDATE ENTITIES  │
│                              706                                    │
└─────────────────────────────────────────────────────────────────────┘
                                  ↓
┌─────────────────────────────────────────────────────────────────────┐
│ SELECT A SET OF ONE OR MORE SIMILAR CANDIDATE ENTITIES FROM THE     │
│ PLURALITY OF CANDIDATE ENTITIES BASED ON APPLICATION OF THE FIRST   │
│                  TRAINED SIMILARITY FUNCTIONK                       │
│                              708                                    │
└─────────────────────────────────────────────────────────────────────┘
                                  ↓
┌─────────────────────────────────────────────────────────────────────┐
│ DISPLAY INFORMATION ASSOCIATED WITH THE FIRST SET OF ONE OR MORE    │
│           SIMILAR CANDIDATE ENTITIES ON THE INTERFACE               │
│                              710                                    │
└─────────────────────────────────────────────────────────────────────┘
```

Fig. 7

LEARNING AND APPLYING CONTEXTUAL SIMILARITIES BETWEEN ENTITIES

CROSS-REFERENCE TO RELATED APPLICATION

The present application claims priority to and benefit of both U.S. Provisional Application No. 62/487,720, filed Apr. 20, 2017, and U.S. Provisional Application No. 62/608,878, filed Dec. 21, 2017, their entirety of which are hereby incorporated by reference herein.

TECHNICAL FIELD

Various embodiments described herein are directed generally to entity data analysis. More particularly, but not exclusively, various methods and apparatus disclosed herein relate to techniques for learning and applying entity contextual similarities.

BACKGROUND

Various clinical decision support ("CDS") algorithms have been developed to provide risk scores for near-term and/or long-term patient deterioration. These help to better identify high-risk patients and gives a clinician time to appropriately plan a course of interventions. Sometimes this therapy decision-making step is determined by clinical guidelines. However, guidelines are not personalized and cannot account for every possible situation. Instead, the decision is often left to the clinician and he/she must rely on past experience.

SUMMARY

The present disclosure is directed to techniques for learning and applying entity contextual similarities. For example, in various embodiments, techniques described herein may be used by clinicians (e.g., physicians, nurses), caregivers, etc. that are treating a specific patient entity to identify other patients that are similar, particularly in a particular medical context. By identifying other contextually similar patients, the clinician is able to learn what treatments were effective or ineffective, what treatments tended to yield particular outcomes, etc. Various point-of-care therapy decision support tools (e.g., software executed by processor(s)) are described herein that provide clinicians with access to various information about a patient being treated (also referred to herein as the "query patient"), including other patients (e.g., cohorts) that are similar to the query patient in various medical contexts.

In various embodiments, techniques such as artificial intelligence (e.g., deep learning, machine learning, kernel classification, multiple kernel learning, etc.) and/or statistical techniques may be employed to facilitate identification of contextually similar patients. For example, in some embodiments, a plurality (or "pool") of "template similarity functions" may be generated. Each template similarity function of the pool of template similarity functions may compare some subset of a feature vector associated with a query patient with a corresponding subset of feature vector(s) associated with one or more other patients, which will be referred to herein as "candidate patients." Entities such as patients may have states that change over time. Accordingly, an entity feature vector such as a query patient feature vector may be considered a "snapshot" of the entity's state during a particular moment or window of time. For example, as time goes on and a patient undergoes more tests, treatments, measurements, etc., a feature vector of the patient may similarly change over time.

In some embodiments, each template similarity function may be designed or "tuned" to determine how similar two patients are with respect to a given feature subset of feature vectors associated with the patients. Consequently, the shape of each template similarity function may be guided by population statistics (e.g., distribution) associated with the feature subsets being compared. These population statistics may be derived, for instance, from a retrospective patient database. In some embodiments, one or more of the template similarity functions may be tuned to highlight or amplify similarities between patients that share abnormal values, such as outlying values that fall towards "tails" of distributions of the particular features. In the aggregate, the pool of template similarity functions may provide a diversified view of similarity between two patients.

In some embodiments, outputs from the pool of template similarity functions may be provided as input (e.g., applied across) to what will be referred to herein as a "a composite similarity function." In some embodiments, a composite similarity function may compute what will be referred to herein as a "composite similarity score" of the query patient and a candidate patient based on the outputs of the pool of template similarity functions. In various embodiments, the composite similarity function may take the form of a machine learning model, a deep learning model, a statistical model, etc. In some embodiments, the composite similarity function may compute a convex combination of the outputs of the pool of template similarity functions.

In some embodiments, the composite similarity function may take the form of a weighted combination of respective outputs of the plurality of template similarity functions. Different sets of weights may be applied to the template similarity function outputs in different contexts. For example, a first set of weights may be applied in a hemodynamic instability context, a second set of weights may be applied in an acute kidney injury context, and so on. The weights applied in a particular medical context may be tuned to amplify outputs of individual template similarity functions that are relatively important to that context. Other outputs of less importance in the medical context may be weighted less heavily.

Weights may be learned in various ways. In some embodiments, the weights may be learned using one or more multiple kernel learning techniques, such as a kernel-smoothing algorithm. Learning these weights, or in other words, training a context-specific version of the composite similarity function, may be based on training data that is labeled for a particular medical context. For example, to learn weights for a hemodynamic instability context, training data that is labeled with some measure of hemodynamic instability may be applied. To learn weights for an acute kidney injury context, training data that is labeled with some measure of acute kidney injury may be applied. And so on.

Once weights are learned for a variety of medical contexts, the pool of template similarity functions and composite similarity function may be applied to feature vectors of a query patient and one or more candidate patients to identify similar candidate patients in a variety of contexts. For example, a ranked list of candidate patients that are most similar to a query patient in a hemodynamic instability context may be determined and provided. In some embodiments, this ranked list could be used, for instance, to identify a "cohort" of contextually similar patients. Clinicians can then evaluate treatments applied to the cohort of similar patients, and resulting outcomes, to more intelligently select a treatment for the query patient. Additionally or alternatively, in some embodiments, a query patient's clinical state in a particular context may be predicted using the pool of template similarity functions and the composite similarity function, e.g., by selecting weights associated with a context of interest.

While examples described herein relate to health care, this is not meant to be limiting. Techniques described herein may be applied in a variety of domains outside of health care. For example, techniques described herein may be used to identify contextually similar entities to an individual in need of rehabilitation for drug and/or alcohol abuse, e.g., so that outcomes for contextually-similar individuals can be learned and leveraged to select a rehabilitation plan. Techniques described herein may also be used in other domains, such as travelling (e.g., identifying others with similar tastes to select an itinerary most likely to be enjoyable), sports (e.g., comparing athletes for team selection), etc.

Additionally, techniques described herein give rise to a variety of technical advantages. For example, by tuning template similarity functions as described herein, it is possible to avoid an imputation approach to missing data because the template similarity functions may only contribute to output of a composite similarity function if values are present. Eliminating the need for data imputation may reduce inaccuracy and/or conserve computing resources such as processor cycles, memory, etc. Moreover, employment of the composite similarity function, particular with different weights learned for different contexts, may effectively impose a sparsifying regularizer (e.g., L1-norm) that allows for template similarities that do not improve performance to be disregarded. In the health care domain, accurately identifying cohorts of contextually similarity, and particularly being able to evaluate treatments and/or outcomes of the cohort, may facilitate more intelligent and/or efficient clinical decision making.

Generally, in one aspect, a method may include the following operations: providing a plurality of template similarity functions, wherein each template similarity function of the plurality of template similarity functions compares a respective subset of features of a query entity feature vector with a corresponding subset of features of a candidate entity feature vector; providing a composite similarity function as a weighted combination of respective outputs of the plurality of template similarity functions; providing a first plurality of labeled entity vectors as first context training data; applying an approximation function to approximate, for each respective labeled entity vector of the first context training data, a first context label for the respective labeled entity vector data based on output the composite similarity function and respective first context labels of the other labeled entity vectors of the first context training data; and training a first context specific composite similarity function based on the composite similarity function, wherein training the first context specific composite similarity function includes learning first context weights for the plurality of template similarity functions using a first loss function based on output of application of the approximation function to the first context training data, wherein the first weights are stored for use as part of the first context-specific composite similarity function.

In various embodiments, the method may further include: providing a second plurality of labeled entity vectors as second context training data; applying the approximation function to approximate, for each respective labeled entity vector of the second context training data, a second context label for the respective labeled entity vector data based on output of the composite similarity function and respective second context labels of the other labeled entity vectors of the second context training data; and training a second context specific composite similarity function based on the composite similarity function, wherein training the second context specific composite similarity function includes learning second context weights for the plurality of template similarity functions using a second loss function based on output of application of the approximation function to the second context training data, wherein the second weights are stored for use as part of the second context-specific composite similarity function.

In various embodiments, the first context-specific composite similarity function may be applicable to a subsequent query entity feature vector and a candidate entity feature vector to determine a similarity measure between the subsequent entity feature vector and the candidate entity feature vector in a first medical context. In various embodiments, the second context-specific composite similarity function may be applicable to the subsequent query entity feature vector and the candidate entity feature vector to determine another similarity measure between the subsequent entity feature vector and the candidate entity feature vector in a second medical context that is different than the first medical context.

In various embodiments, the first medical context may include hemodynamic stability. In various embodiments, the second medical context may include acute kidney injury. In various embodiments, providing the plurality of template similarity functions may include: selecting at least one feature shared by the query entity feature and the candidate entity feature vector; determining a population distribution for the selected feature across the plurality of candidate entities; and generating a given template similarity function of the plurality of template similarity functions that computes a cumulative probability score of any entity having a selected feature value between a selected feature value of the query entity feature vector and a selected feature value of the candidate entity feature vector according to the population distribution.

In various embodiments, the given template similarity function may be further normalized based on an average similarity score of at least one of the query entity feature vector and the candidate entity feature vector to other entities across the population distribution. In various embodiments, the approximation function may include a kernel-smoothing function.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

FIGS. 3, 4, and 5 depict example graphical user interfaces that may present information determined using techniques described herein.

FIGS. 6 and 7 depict example methods for implementing selected aspects of the present disclosure.

DETAILED DESCRIPTION

Various clinical decision support ("CDS") algorithms have been developed to provide risk scores for near-term and/or long-term patient deterioration. These help to better identify high-risk patients and gives a clinician time to appropriately plan a course of interventions. Sometimes this therapy decision-making step is determined by clinical guidelines. However, guidelines are not personalized and cannot account for every possible situation. Instead, the decision is often left to the clinician and he/she must rely on past experience. In general, it would be beneficial to be able to determine contextual similarities between entities such as patients for a variety of purposes in a variety of domains.

Figure 1:
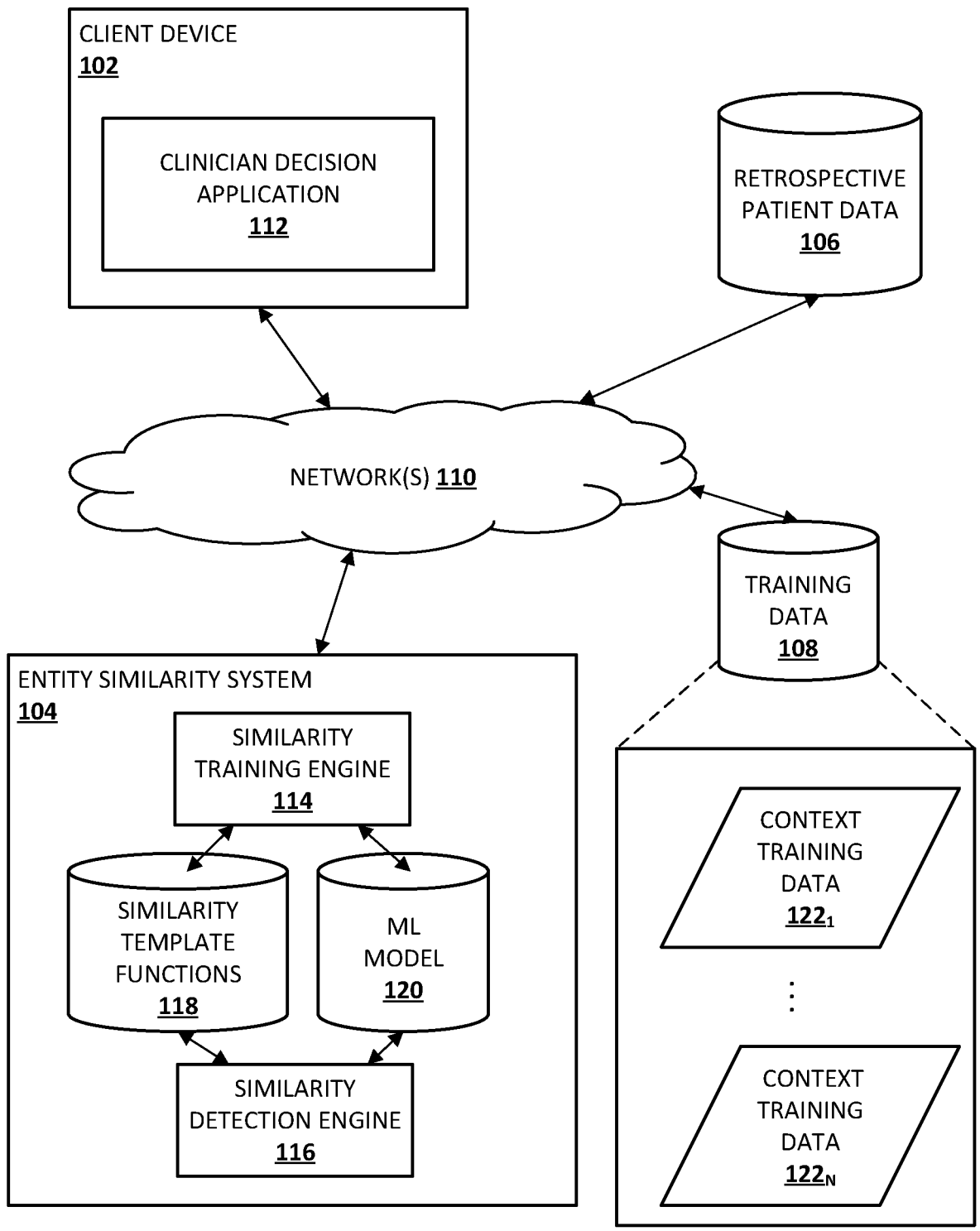
FIG. 1 illustrates schematically an environment in which selected aspects of the present disclosure may be implemented, in accordance with various embodiments.

In view of the foregoing, various embodiments and implementations of the present disclosure are directed to learning and applying entity contextual similarities. Referring to FIG. 1, an environment in which selected aspects of the present disclosure may be implemented is depicted schematically. One or more client devices 102, an entity similarity system 104, a retrospective patient database 106, and a training database 108 are shown in network communication via one or more networks 110, such as the Internet. In various embodiments, one or more of components 102-108 may be omitted, combined with other components, and other components may or may not be added.

The one or more client devices 102 may include, for example, one or more of: a desktop computing device, a laptop computing device, a tablet computing device, a mobile phone computing device, a computing device of a vehicle of the user (e.g., an in-vehicle communications system, an in-vehicle entertainment system, an in-vehicle navigation system), a standalone interactive speaker, a smart appliance such as a smart television, and/or a wearable apparatus of the user that includes a computing device (e.g., a watch of the user having a computing device, glasses of the user having a computing device, a virtual or augmented reality computing device). Additional and/or alternative client computing devices may be provided.

Figure 4:
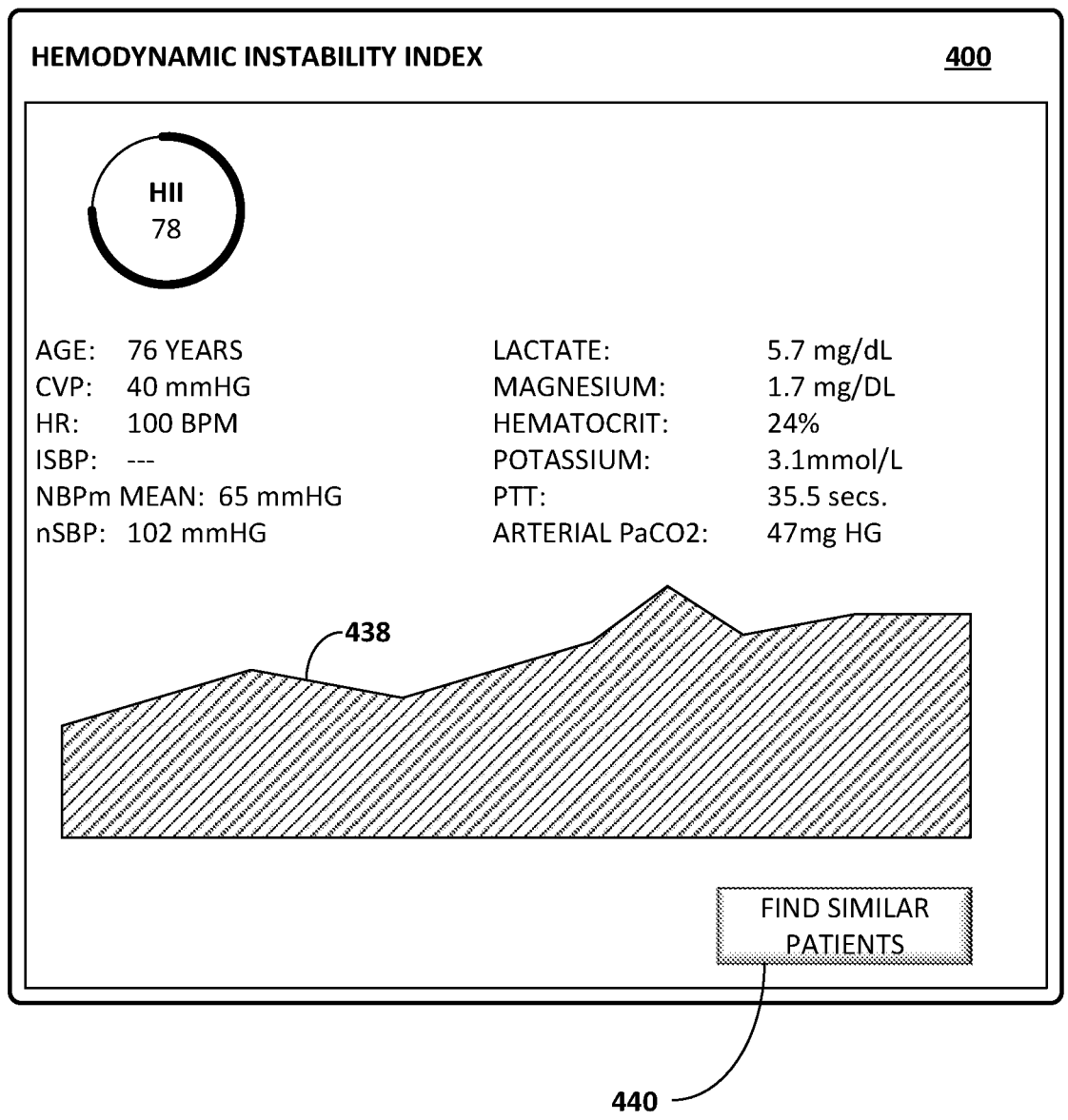
Figure 5:
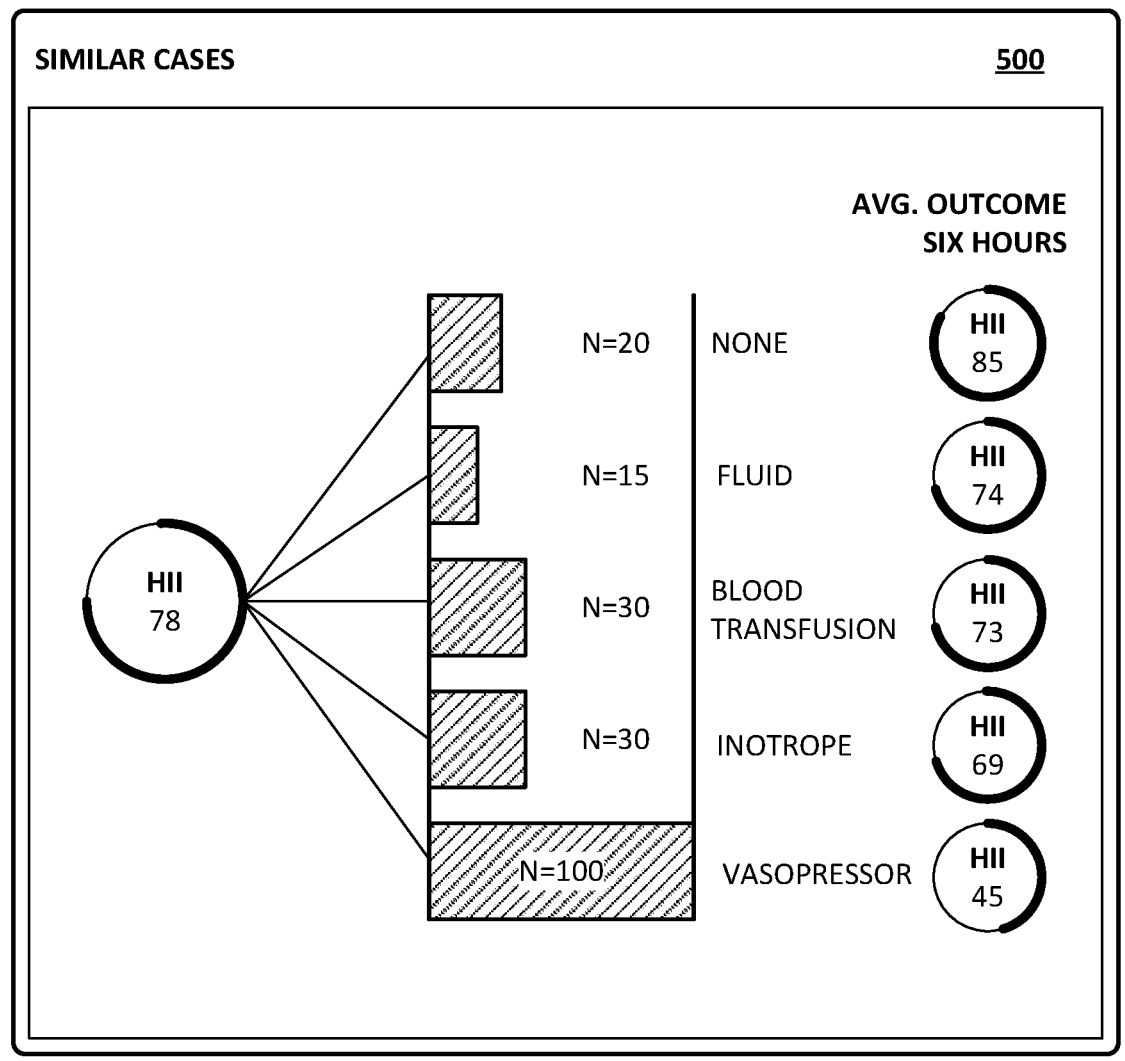

In various embodiments, client device(s) 102 may operate a variety of different applications, such as a web browser, an email client, a messaging client, a social media client, etc. Most importantly for the present disclosure, client device 102 (which will be referred to hereon in the singular) may operate a clinician decision application 112. Clinician decision application 112 may be software that is operable, e.g., by a clinician or another individual interested in a particular patient's condition (e.g., a caregiver, researcher, etc.), to evaluate information determined using various aspects of the present disclosure. FIGS. 3-5 depict example graphical user interfaces ("GUIs") that may be generated and/or presented by clinician decision application 112, in accordance with various embodiments.

Entity similarity system 104 may include one or more computing devices that may operate collectively to collect, generate, and/or compute data that is usable to identify contextually similar entities, which in this example and other described herein may be medical patients. In some embodiments, entity similarity system 104 may include one or more modules or engines, any of which may be implemented using any combination of hardware and/or software. In FIG. 1, for instance, entity similarity system 104 includes a similarity training engine 114 and a similarity detection engine 116. In other embodiments, engines 114 and 116 may be combined into a single engine or module. In some embodiments, and as will be described in more detail below, entity similarity system 104 may employ a plurality of similarity template functions 118 and/or one or more machine learning models 120 to compute contextual similarities between entities such as patients.

Retrospective patient database 106 may include information about patients, such as ages, weights, diagnoses, vital signs, tests performed, test results, treatments prescribed/applied, medications, etc. In some embodiments, retrospective patient database 106 may take the form of a convention hospital information system ("HIS") that is used to store, for instance, electronic medical records ("EMRs") associated with a plurality of patients. As will be described in more detail shortly, patient records in retrospective patient database 106, and in some cases, feature vectors generated/extracted from those records, may be used to represent candidate patients for performance of techniques described herein. While depicted as a single database in FIG. 1, retrospective patient database 106 (and any other database or index described herein) may in reality be implemented using any number of databases, which may be operated by one or more computing systems, such as a group of computing systems that cooperate to provide a so-called "cloud" computing system or architecture.

Training database 108 may store one or more context training data sets $122_{1-N}$ that are used, for instance, to train machine learning model(s) 120. In some embodiments, training database 108 and retrospective patient database 106 may be combined into a single logical and/or physical database. In some embodiments, multiple context training data sets $122_{1-N}$ may be stored in training database 108. As will be described in more detail shortly, in some embodiments, each set of context training data 122 may including individual training examples that are labeled with particular context labels. These labels may facilitate training, for instance, of distinct instances of machine learning model 120 that are usable in distinct contexts. As an example, individual training examples of a first context training data set $122_1$ may be labeled to indicate a measure or indication of hemodynamic instability. Individual training examples of a second context training data set $122_2$ may be labeled to indicate a measure of acute kidney injury. And so on. In some embodiments, the labels may be binary, e.g., to indicate presence or absence of a particular medical condition. Additionally or alternatively, the labels may be non-binary, and may instead indicate a measure (e.g., within a continuous range) of a particular feature value.

Entity similarity system 104 may be configured to perform various aspects of the present disclosure, e.g., by way of similarity training engine 114 and/or similarity detection engine 116. For example, in some embodiments, entity similarity system 104 may be configured to provide/obtain a plurality of template similarity functions 118. Each template similarity function of the plurality of template similarity functions 118 may compare a respective subset of features of a query entity feature vector (e.g., a query patient feature vector) with a corresponding subset of features of a candidate entity feature vector (e.g., a candidate patient feature vector).

In some embodiments, entity similarity system 104 may also include the aforementioned mentioned machine learning model(s) 120 that receives outputs of the template similarity functions 118 as input and computes, based on those values, a composite similarity score. In some embodiments, each machine learning model 120 may take the form of a composite similarity function, which in some embodiments may be a weighted combination of respective outputs of the plurality of template similarity functions 118.

In various embodiments, similarity training engine 114 may be configured to obtain, e.g., from training database 108, a first plurality of labeled entity vectors as first context training data. For example, if machine learning model 120 is being trained to compute similarities between patients in the hemodynamic instability context, similarity training engine 114 may obtain a context training data set 122 that includes training examples that are labeled to indicate hemodynamic stability (or lack thereof). As will be described in more detail below, similarity training engine 114 may train machine learning model 120 using these training examples in order to tune machine learning model 120 to compute similarities between patients in the hemodynamic instability context. In various embodiments, multiple machine learning models 120 may be trained, e.g., one for each desired context. For example, one machine learning model 120 may be trained for computing similarity between patients in the hemodynamic instability context. Another may be trained for computing similarity between patients in the acute kidney injury context. And so on.

Similarity detection engine 116 may be configured to apply a query entity feature vector, which may include a plurality of features extracted from the entity, to one or more candidate entity feature vectors, e.g., using similarity template functions 118 and one or more trained machine learning models 120. In the medical context, for instance, similarity detection engine 116 may be configured to compare features of a query patient, such as vital signs, age, weight, treatments, etc. (which may be obtained in real time and/or from retrospective patient database 106) with corresponding features of a candidate patient that are obtained from retrospective patient database 106, using similarity template functions 118 and machine learning model 120. As output, similarity detection engine 116 may simply provide a contextual similarity score between the query entity and the candidate entity, or, it may provide a list of candidate entities that is ranked based on similarity to the query entity.

Output of similarity detection engine 116 may be used by clinician decision application 112 to provide clinicians or other personnel with information and/or tools that enable the clinician to make informed decision about the query patient. As a non-limiting example, a clinician may be able to view a cohort of contextually similar patients to see what treatments were applied, as well as the (e.g., statistical) outcomes of those treatments. Based on this information, the clinician may decide a course of action. Additionally or alternatively, in some embodiments in which treatments are administered automatically, e.g., by robots, the treatment applied may be selected automatically based at least in part on information provided by similarity detection engine 116. As another example, clinician decision application 112 may predict a query patient's clinical state in a particular context using techniques described herein.

Template Similarity Functions

One technique for generating template similarity functions 118 will now be described. It should be understood that this description is not meant to be limiting, and other techniques and/or template similarity functions may be employed. And while the phrase "template similarity function" is used herein, this is not meant to be limiting. These functions may also be referred to as "kernels." For purposes of this discussion, the query patient—e.g., the patient for which a clinician wishes to make a decision regarding treatment, etc.—may be denoted as $p_q$, and each candidate patient to which $p_q$ is compared may be denoted $p_c$.

In some embodiments, a pool of m template similarity functions $S_1(p_q, p_c), \ldots, S_m(p_q, p_c)$ may be generated. These may serve as a basis for the subsequent contextual similarity learning phase described below. Each of the template similarity functions $S_i(p_q, p_c)$ takes as input two feature vectors—one from the query patient $p_q$ and one from a candidate patient $p_c$—and returns output (e.g., a score) that quantifies a degree of similarity between $p_q$ and $p_c$. Each template similarity function judges similarity in a different way by considering different subsets of the patients' feature vectors. For example, each template similarity function may be tuned to a different feature, e.g., a similarity function based on heart rate or blood pressure. It is also possible to consider small groups of features to address interactions between features. The resulting pool of template similarity functions $S_i(p_q, p_c), \ldots, S_m(p_q, p_c)$ may provide a diversified view of similarity. This diversified view may be fused into a single score based on the clinical context using a context-specific machine learning model 120 (described in more detail below).

Figure 2:
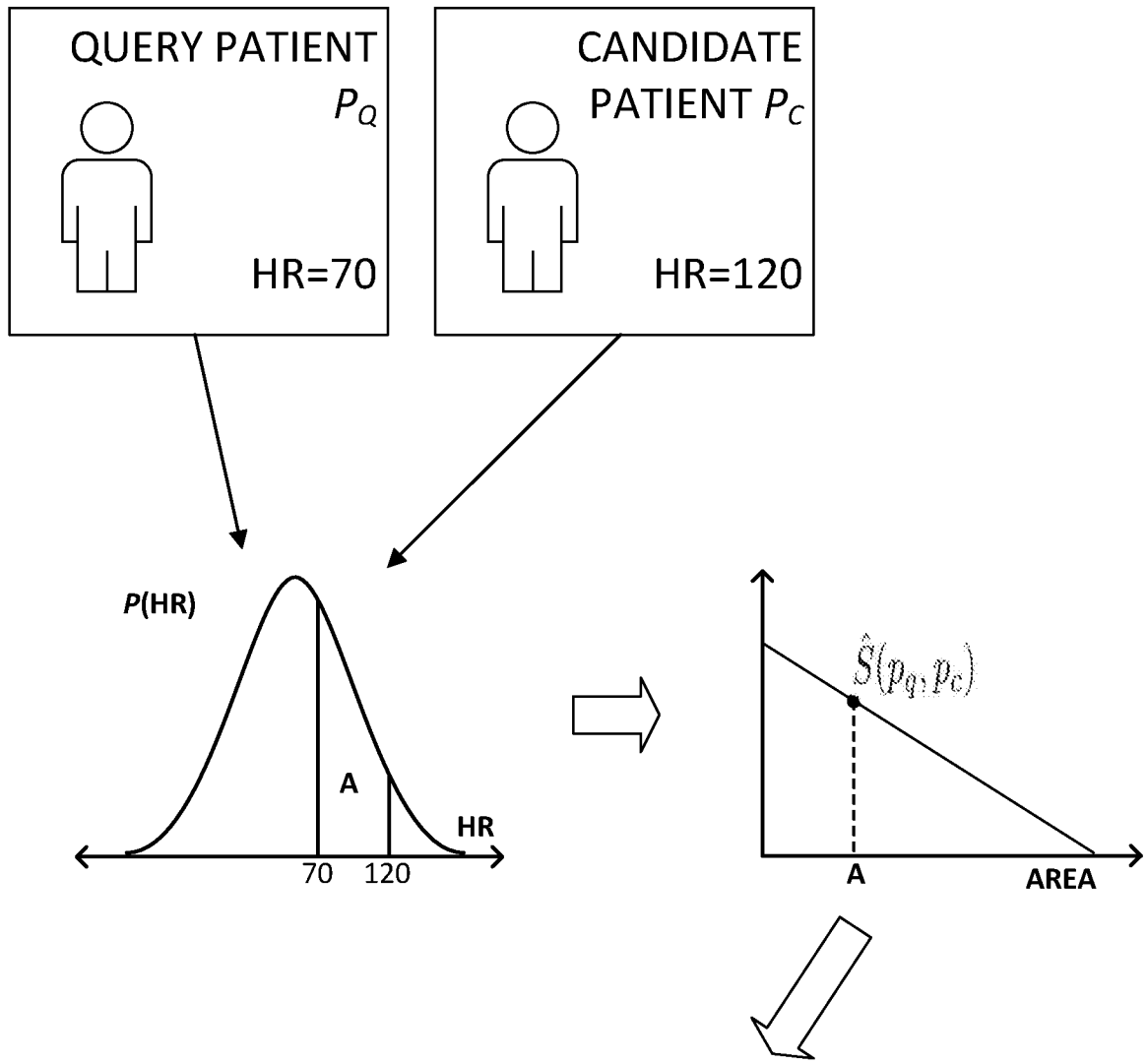
FIG. 2 demonstrates on technique for generating template similarity functions, in accordance with various embodiments.

FIG. 2 demonstrates an example of how a single template similarity function may be applied for a particular patient feature, namely, heartrate. Other template similarity functions that evaluate other types of similarities between other patient vector features may operate similarly. In various embodiments, a population distribution may be determined for patient heartrates. This can be achieved, for instance, by computing a histogram of heartrates from a set of training data 120 in training database 108.

In this example, the query patient $p_q$ has a heartrate ("HR") of 70 and the candidate patient $p_c$ has a heartrate of 120. Arrows from the query patient and candidate patient lead to a histogram demonstrating a distribution of patient heartrates, which resembles a bell curve (although this is not required). Such a histogram may provide a probability distribution $P_{HR}(x)$. In some embodiments, an un-normalized template similarity function may be computed using an equation such as the following:

$$\hat{S}(p_q, p_c) = f(P_{HR}(p_q \leq HR \leq p_c)) \qquad (1)$$

In some embodiments, the function $f$ may be a monotonically decreasing function, e.g., $f(x)=(1-x)$. In this example, $P_{HR}(x_q \leq HR \leq x_c)$ may be a cumulative probability of a patient having a heartrate somewhere between those of $p_q$ and $p_c$. Because the function $f$ is monotonically decreasing, the similarity between respective heartrates of $p_q$ and $p_c$ decreases (or increases) as the cumulative probability increases (or decreases). The cumulative probability is represented by the area A depicted under the bell curve in FIG. 2.

In some embodiments, the template similarity function may be normalized using an equation such as the following:

$$S(p_q, p_c) = \frac{\hat{S}(p_q, p_c)}{\sqrt{E[\hat{S}(p_q, \cdot)]}\sqrt{E[\hat{S}(p_c, \cdot)]}} \qquad (2)$$

In equation (2), the denominator terms represent the expected average un-normalized template similarity function outputs of $p_q$ and $p_c$, respectively, to all other patients in retrospective patient database 106. E stands for expectation (mean value). This normalization may serve to normalize the outputs of the template similarity function into a common range.

This approach uses the population distribution or a cohort population distribution of the feature in order to quantify similarity. The effect of this procedure is that a similarity between two heartrate values for $p_q$ and $p_c$ is determined both by how close they are, but also by how abnormal they are. Since the similarity score is inversely proportional to the area (A in FIG. 2) under the probability distribution between the two values, abnormal values, which are located closer to the tails of the distribution, will receive a higher score. This has the benefit of highlighting abnormal values that a clinician may be concerned about. Intuitively, given two patients (or more generally, two entities), their similarity is inversely related to the expected number of patients (or more generally, entities) that lie between them.

While this heartrate example applies for a single feature (heartrate) being compared between patients, this is not meant to be limiting. These steps can be generalized to template similarity measures that consider multiple features of patient (or more generally, entity) vectors. In particular, a multidimensional probability distribution may be employed.

Generally speaking, template similarity vectors, or "kernels," may be generated in various ways. For example, denote $x_j$ and $z_j$ as the corresponding feature values for two entities with state vectors x and z. Then the expected number of entities with values in the range $[\min(x_j, z_j), \max(x_j, z_j)]$ is given by the area under the population distribution, $P(X_j)$, for $X_j$ in that interval. In some embodiments, the following kernel may be employed on feature $X_j$:

$$k_{j,c}(x,z) = (1 - P(\min(x_j, z_j) \leq X_j \leq \max(x_j, z_j)))^c \qquad (A)$$

In various embodiments, a kernel may be applied to binary or ordinal discrete features. For example, $X_j$ may be a Bernoulli random variable characterizing whether or not a patient exhibits a symptom or presents with a rare condition or comorbidity. In this case, Equation (A) simplifies to:

$$k_{j,c}(x,z) = \begin{cases} (1 - P(X_j = 1))^c & , x_j = z_j = 1 \\ (1 - P(X_j = 1))^c & , x_j = z_j = 1 \\ 0 & , x_j \neq z_j \end{cases}$$

Thus, the similarity between patients x and z may be inversely related to the prevalence or absence of the clinical condition if both patients have or don't have the condition, and there may be no similarity if they differ in condition status. The above-described kernel assumes an ordinal relation to the values of the random variable. However, it can be extended to nominal categorical variables by one-hot encoding, which converts a nominal variable on c categories into c Bernoulli random variables.

Machine Learning Model Training

An example technique for training machine learning model(s) 120 to generate a composite similarity score based on aggregated outputs of the m template similarity functions 118 will now be described. In some embodiments, machine learning model 120 may be a composite similarity function, $S_C(p_q, p_c)$, that may be a convex combination of the m template similarity function outputs. For example, in some embodiments, the composite similarity function may be modeled as follows:

$$S_C(p_q, p_c) = \sum_{i=1}^{m} a_i S_i(p_q, p_c) \qquad (3)$$

$$\text{subject to } a_i \geq 0, i = 1, \ldots, m \qquad (4)$$

$$\sum_{i=1}^{m} a_i = 1 \qquad (5)$$

Thus, $S_C$ in this example is a weighted average of the m individual template similarity function outputs, with the weights being denoted $a_1, a_2, \ldots, a_m$.

In order to train machine learning model 120, which may mean, for instance, learning the weights $a_1, a_2, \ldots, a_m$, in various embodiments, n paired training examples $(p^{(1)}, y^{(1)}), \ldots, (p^{(n)}, y^{(n)})$ may be provided, e.g., from training database 108. $p^{(i)}$ may be a vector of input features for a given patient (vitals, labs, demographics, etc.) and $y^{(i)}$ may be a label that indicates the clinical context state of that patient. The clinical context may be a binary label or real-valued number, depending on the clinical state it is reflecting. For example, $y^{(i)}$ may be a binary label that indicates which of two disease states patient (i) belongs to.

In some embodiments, the weights $a_1, a_2, \ldots, a_m$ may be trained using a multiple kernel learning algorithm, such as a kernel-smoothing algorithm, that is performed on the labeled training set $(p^{(1)}, y^{(1)}), \ldots, (p^{(n)}, y^{(n)})$. For example, in some embodiments, the following approximation function may be employed to compute an approximate label $\hat{y}$ for each patient:

$$\hat{y}^{(i)} = \sum_{j \neq i} S_C(p^{(i)}, p^{(j)}) y^{(i)} \qquad (6)$$

Intuitively, Equation (6) attempts to approximate the label ($\hat{y}$) for the ith patient by taking a weighted average of the "true" labels (y) of neighbors of the ith patient, wherein the neighbors are defined by the composite similarity $S_C$. Thus, if the output of $S_C$ indicates that two neighboring patients are similar, then one neighbor's "true" label (y) will more heavily influence the approximated label ($\hat{y}$) for the other.

Once the approximated labels are computed, differences between the approximated labels and the "true" labels can be used to determine the weights $a_1, a_2, \ldots, a_m$. For example, a loss function $\mathcal{L}(y, \hat{y})$ may be used to measure a discrepancy between a true label y and its approximation $\hat{y}$. For example, if the labels are binary, then binary cross-entropy can be used. If the labels are continuous-valued, then squared error may be used as a loss. In either case, an equation such as the following may be used to minimize the total loss over all the training examples:

$$\sum_{i=1}^{n} \mathcal{L}(y^{(i)}, \hat{y}^{(i)}) \qquad (7)$$

Note that this objective is implicitly a function of the weights $a_1, a_2, \ldots, a_m$ through $S_C$. Minimization may then proceed, e.g., using gradient descent (e.g., stochastic, batch, etc.) to learn the optimal weights in this context.

In some embodiments, Equation (6) may also be used to predict a particular subject's clinical context (i.e., their label) based on "true" labels (y) associated with similar subjects. For example, the label approximation $\hat{y}$ determined for a subject with an unknown clinical status may be influenced by corresponding true labels y associated with subjects that are determined, e.g., using one or more of Equations (3)-(5) described above.

Example of Use

FIGS. 3-5 depict example graphical user interfaces ("GUIs") that may be rendered on a display screen by clinician decision application 112 in FIG. 1. Referring now to FIG. 3, a dashboard GUI 300 may be viewed by a clinician when, for example, the clinician pulls up a query patient's record. In this example, the query patient's name is "John Doe," as indicated in the title bar of dashboard GUI 300. Dashboard GUI 300 enables the clinician to get an overview of the query patient's current clinical state. A number of different panels, four ($330_{1-4}$) which are depicted in FIG. 3, may each convey a context-specific aspect of the query patient's state, such as an overview of a particular anatomical system, a state of a particular condition, etc. For example, a first panel $330_1$ gives an overview of cardiovascular health. A second panel $330_2$ gives an overview of the query patient's cardiorenal syndrome ("CRS"). A third panel $330_3$ gives an overview of the query patient's renal system. A fourth panel $330_4$ gives an overview of the query patient's respiratory system. These panels $330_{1-4}$ are merely examples; more or less panels providing overviews of other clinical contexts may be provided.

A fifth panel $330_5$ is also depicted that provides an overview of various clinician decision support ("CDS") statistics of the query patient. In FIG. 3, this includes an overview of the query patient's hemodynamic instability index, or "HII," as well as overviews of the query patient's acute kidney injury ("AKI") status and acute respiratory distress syndrome ("ARDS"). In FIG. 3, additional information 332 is depicted about the query patient's HII because it is elevated (78).

A clinician may select any of the panels 330, e.g., using a mouse or by touching a touchscreen, to obtain more detailed information about the respective clinical context. For example, given the query patient's elevated HII, a clinician is likely to select the portion of fifth panel $330_5$ that pertains to HII to gain additional information. Upon doing so, another GUI such as GUI 400 depicted in FIG. 4 may be rendered.

In FIG. 4, GUI 400 includes a more detailed overview of the query patient's hemodynamic instability index, including various pieces of data that contributed to the HII score of 78 (e.g., age, CVP, heartrate, etc.). GUI 400 may also include a chart 438 that depicts the query patient's HII over time. Additionally, GUI 400 may include a button 440 or other selectable element that the clinician can select to view similar patients. When selected, this may trigger application of a feature vector associated with the query patient across the plurality of template similarity functions (118 in FIG. 1) to compute respective outputs. As described above, these outputs may be applied as inputs across a context-specific machine learning model 120, which as noted above may be a composite similarity function (e.g., equation (3) above) that applies weights leaned for the current context to the outputs of the template similarity functions to compute a composite contextual similarity score. In particular, weights learned by using a context training data set 122 from training database 108 with the various equations described previously may be applied to the respective outputs of the template similarity functions. In some embodiments, the technique may be applied to compare a plurality of candidate patient feature vectors, e.g., using information from retrospective patient database 106, with the candidate patient's feature vector, and a list of candidate patients ranked by similarity with the query patient may be returned. In some embodiments, only the x most similar patients may be returned, with x being, for example, a positive integer that is manually selected or determined based on a number or percentage of candidate patients that satisfy some similarity threshold.

FIG. 5 depicts one example GUI 500 that may be rendered in response to selection of button 440. In FIG. 5, the query patient's HII score of 78 is depicted with lines connecting it to a plurality of treatment option groups. In FIG. 5 these options include no treatment, fluid treatment, blood transfusion, inotrope, and vasopressor treatments. However, these are not meant to be limiting. For each treatment option group, a number of similar patients for which the respective treatment option was applied is also depicted, along with a respective average outcome, which in this example is an average HII post-treatment.

For instance, no treatment was applied for twenty contextually similar patients, and lead to an increased average HII score of 85. Fluid treatment was applied for fifteen contextually similar patients, and lead to a lightly decreased average HII score of 74. Blood transfusion was applied for thirty contextually similar patients, and lead to a lightly decreased average HII score of 73. Inotrope treatment was applied for thirty contextually similar patients, and lead to a lightly decreased average HII score of 69. Vasopressor treatment was applied for the majority of contextually similar patients, namely, one hundred of them, and lead to a sharply decreased average HII score of 45. Accordingly, the clinician can easily see that vasopressor was by far the most effective treatment option applied for contextually similar patients. In various implementations, each treatment option group may itself be selectable to view more information (e.g., more refined statistics) about the contextually similar patients in that group, as well as treatments they received.

While not depicted in the Figures, in various embodiments, techniques described herein may be implemented to provide clinicians with other information besides that depicted in FIG. 5. For example, in some embodiments, a clinician may be presented with some number of most contextually similar patients, e.g., as a list. In some such embodiments, the clinician may be able to select a given contextually similar patient to learn more about the contextually-similar patient, such as their medical history, specific measurements (e.g., vital signs, lab results), treatments applied/prescribed, family history, etc.

Figure 6:
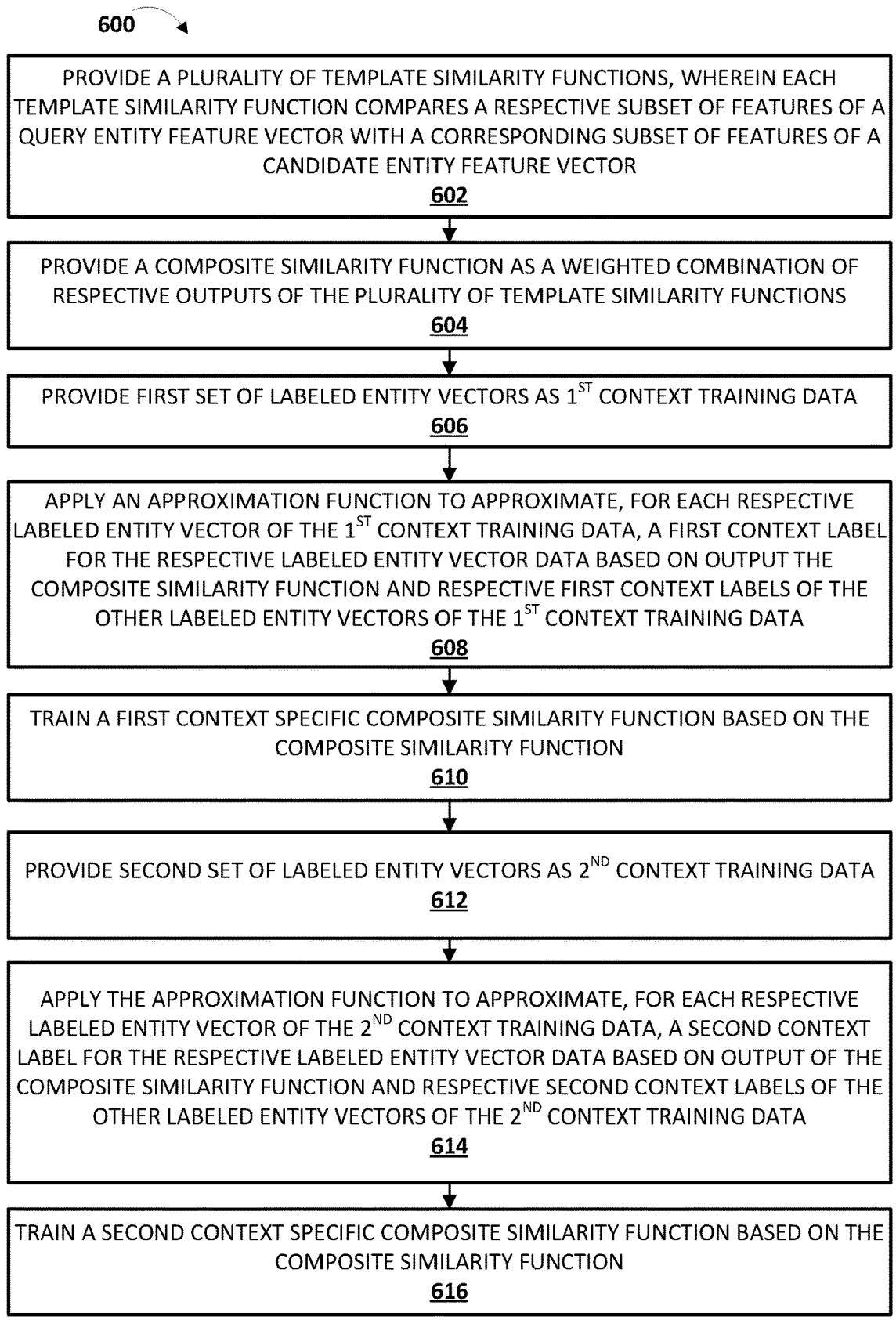

FIG. 6 depicts an example method 600 for practicing selected aspects of the present disclosure, in accordance with various embodiments. For convenience, the operations of the flow chart are described with reference to a system that performs the operations. This system may include various components of various computer systems, including entity similarity system 104. Moreover, while operations of method 600 are shown in a particular order, this is not meant to be limiting. One or more operations may be reordered, omitted or added. In addition, other mid-range or long-term outcomes, such as rate of organ failure, length of stay, mortality, etc., may also be displayed.

At block 602, the system may provide a plurality of template similarity functions, e.g., 118 in FIG. 1. The plurality of template functions may be provided in various ways. In some embodiments, they may be created manually, e.g., by one or more clinicians. As noted above, each template similarity function of the plurality of template similarity functions may be designed to compare a respective subset of features of a query entity feature vector associated with a query patient with a corresponding subset of features of a candidate entity feature vector associated with a candidate patient. At block 604, the system may provide a machine learning model, such as a composite similarity function that includes a weighted combination of respective outputs of the plurality of template similarity functions. Equation (3) above is one non-limiting example of a composite similarity function.

At block 606, the system may provide and/or obtain, e.g., from training database 108, a first plurality of labeled entity vectors as first context training data (e.g., 120$_1$ in FIG. 1). In some embodiments, this first context training data may be specifically selected to train weights for a composite similarity function that is to be applied to find similar entities (e.g., patients) in a particular context. For example, if the goal is to find patients similar to any patient diagnosed with Type II diabetes, then the first context training data may include training examples in the form of patient feature vectors that are labeled to indicate absence or presence of Type II diabetes.

At block 608, the system, e.g., by way of similarity training engine 114, may apply an approximation function such as Equation (6) above to approximate, for each respective labeled entity vector of the first context training data, a first context label ($\hat{y}$) for the respective labeled entity vector data. In some embodiments, the first context label may be approximated based on output of the composite similarity function and respective "true" first context labels (y) of the other labeled entity vectors of the first context training data. As noted above, intuitively this may mean that the more two patients are similar, the more a true label (y) of one patient will contribute to an approximated label ($\hat{y}$) of the other, and vice versa.

At block 610, the system may train a first context specific composite similarity function based on the composite similarity function (e.g., equation (3) described previously). This may include, for instance, learning first context weights $a_1$, $a_2$, . . . , $a_m$ for the plurality of template similarity functions (e.g., 118 in FIG. 1) using a first loss function (e.g., $\mathcal{L}(y,\hat{y})$) based on output of application of the approximation function (e.g., Equation (6) described previously) to the first context training data. In various embodiments, the first weights may be stored for later use as part of the first context-specific composite similarity function.

As described previously, in various embodiments, different context specific composite similarity functions (or more generally, machine learning models 120) may be learned for different entity contexts. For example, a first context specific composite similarity function may be learned for hemodynamic instability, a second for acute kidney injury, a third for one type of cancer, a fourth for another type of cancer, a fifth for type I diabetes, a sixth for type II diabetes, and so on. Accordingly, at block 612, the system may provide a second plurality of labeled entity vectors as second context training data, similar to block 606.

At block 614, the system may apply the approximation function (e.g., Equation (6) described previously) to approximate, for each respective labeled entity vector of the second context training data, a second context label for the respective labeled entity vector data based on output of the composite similarity function and respective second context labels of the other labeled entity vectors of the second context training data. This operation may be similar to block 608. At block 616, the system may train a second context specific composite similarity function based on the composite similarity function, similar to block 610. In some embodiments, blocks 606-610 may be repeated for as many different contexts as desired, resulting in a "library" of context-specific composite similarity functions that can be selectively applied later to find contextually similar entities and/or predict a query entity's state in a particular context.

FIG. 7 depicts an example method 700 for practicing selected aspects of the present disclosure, namely, applying the template similarity functions and context-specific machine learning model(s) (e.g., composite similarity functions) learned using operations such as those depicted in FIG. 6 to identify contextually similar entities. For convenience, the operations of the flow chart are described with reference to a system that performs the operations. This system may include various components of various computer systems, including entity similarity system 104 and/or clinician decision application 112. Moreover, while operations of method 700 are shown in a particular order, this is not meant to be limiting. One or more operations may be reordered, omitted or added.

At block 702, the system may display, on an interface, a first value for a query entity. In various embodiments, the first value may be related to a first context, and the first query entity may be an entity of interest, such as a query patient being examined by a clinician. Examples of first values related to a first context were depicted in FIGS. 3-4, with the context being hemodynamic instability, and the value being an HII score of 78. At block 704, the system may select, from a plurality of trained similarity functions, a first trained similarity function that is associated with the first context. The trained similarity functions may include, for instance, context-specific composite similarity functions that were learned using the operations of FIG. 6. As an example, when a clinician selects button 440 in FIG. 4, that may trigger selection of a context-specific composite similarity function trained for hemodynamic instability. In particular, the selected context-specific composite similarity function may include weights specific to hemodynamic instability that were learned using equations such as Equations (6)-(7) described previously.

At block 706, the system may apply the first selected trained similarity function to a set of features associated with the query entity and respective sets of features associated with a plurality of candidate entities. For example, a query patient feature vector may include features such as demographics (e.g., age, weight, gender, etc.), comorbidities, vital signs (e.g., heartrate, systolic blood pressure, etc.), and/or lab results (e.g., sodium, lactate, magnesium, etc.). A candidate patient feature vector may be selected from retrospective patient database 106 and may include similar features. In some embodiments, a patient feature vector (query or candidate) may include features extracted from a latent variable model, such as features extracted from a hidden layer in a deep neural network. In various embodiments, the query patient feature vector and candidate patient feature vector may be applied as input to the pool of template similarity functions 118. The respective outputs of these functions may be applied as input to the machine learning model 120, which as noted previously may be a similarity function, such as the composite similarity function of Equation (3), that has been trained for the selected context.

At block 708, the system may select a set of one or more similar candidate entities from the plurality of candidate entities based on application of the first trained similarity function at block 706. For example, in some embodiments, the system may return a list of candidate patients that are ranked by contextual similarity to the query patient. At block 710, the system, e.g., by way of clinician decision application 112, may display information associated with the first set of one or more similar candidate entities on the interface.

The information displayed at block 710 may take various forms. In some embodiments it may include, for instance, distinct panels for each returned contextually-similar candidate patient. Each panel may display various context-specific information about the respective candidate patient. In some embodiments, a panel may be selected by a clinician to display more detailed information about the respective candidate patient. Additionally or alternatively, this information may include various statistics about the contextually-similar patients, such as statistics relating to treatments, outcomes, etc. among groups of contextually-similar patients that are grouped by attributes such as outcomes, treatments applied, etc. An example of such statistics was depicted in FIG. 5.

Figure 8:
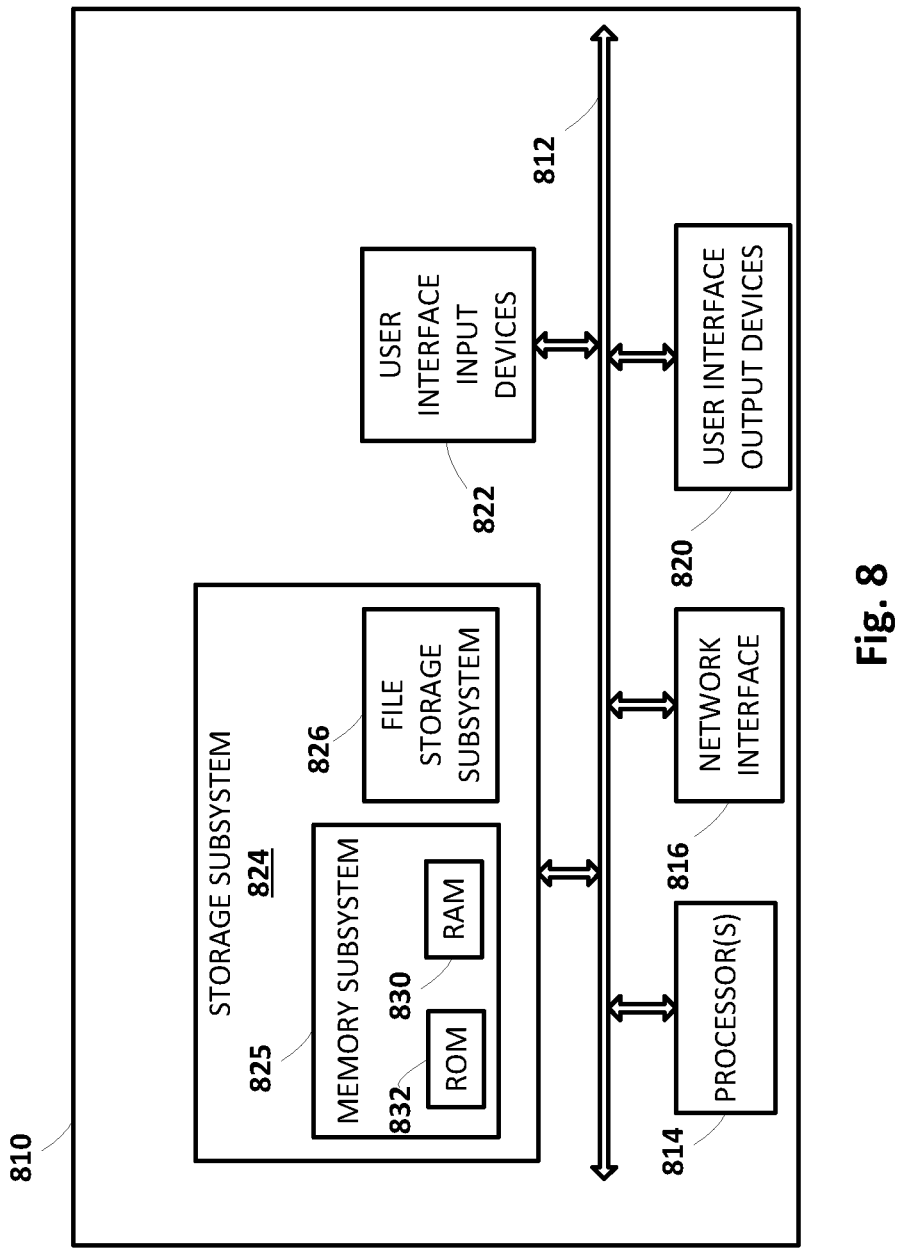
FIG. 8 schematically depicts an example computing system architecture.

FIG. 8 is a block diagram of an example computer system 810. Computer system 810 typically includes at least one processor 814 which communicates with a number of peripheral devices via bus subsystem 812. These peripheral devices may include a storage subsystem 824, including, for example, a memory subsystem 825 and a file storage subsystem 826, user interface output devices 820, user interface input devices 822, and a network interface subsystem 816. The input and output devices allow user interaction with computer system 810. Network interface subsystem 816 provides an interface to outside networks and is coupled to corresponding interface devices in other computer systems.

User interface input devices 822 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 810 or onto a communication network.

User interface output devices 820 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 810 to the subject or to another machine or computer system.

Storage subsystem 824 stores programming and data constructs that provide the functionality of some or all of the modules/engines described herein. For example, the storage subsystem 824 may include the logic to perform selected aspects of methods 600 and/or 700, and/or to implement one or more components depicted in the various figures. Memory 825 used in the storage subsystem 824 can include a number of memories including a main random access memory (RAM) 830 for storage of instructions and data during program execution and a read only memory (ROM) 832 in which fixed instructions are stored. A file storage subsystem 826 can provide persistent storage for program and data files, and may include a hard disk drive, a CD-ROM drive, an optical drive, or removable media cartridges. Modules implementing the functionality of certain implementations may be stored by file storage subsystem 826 in the storage subsystem 824, or in other machines accessible by the processor(s) 814.

Bus subsystem 812 provides a mechanism for letting the various components and subsystems of computer system 810 communicate with each other as intended. Although bus subsystem 812 is shown schematically as a single bus, alternative implementations of the bus subsystem may use multiple busses.

Computer system 810 can be of varying types including a workstation, server, computing cluster, blade server, server farm, smart phone, smart watch, smart glasses, set top box, tablet computer, laptop, or any other data processing system or computing device. Due to the ever-changing nature of computers and networks, the description of computer system 810 depicted in FIG. 8 is intended only as a specific example for purposes of illustrating some implementations. Many other configurations of computer system 810 are possible having more or fewer components than the computer system depicted in FIG. 8.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method of training and applying a context-specific model for determining similarity using a comparison system, the method comprising:
providing a plurality of template similarity functions, wherein each template similarity function of the plurality of template similarity functions compares a respective subset of features of a query entity feature vector with a corresponding subset of features of a candidate entity feature vector;
providing a composite similarity function as a weighted combination of respective outputs of the plurality of template similarity functions;
providing a first plurality of labeled entity vectors as first context training data;
applying an approximation function to approximate, for each respective labeled entity vector of the first context training data, a first context label for the respective labeled entity vector data based on an output of the composite similarity function and respective first context labels of the other labeled entity vectors of the first context training data;
training a first context specific composite similarity function based on the composite similarity function, wherein training the first context specific composite similarity function includes learning first context weights for the plurality of template similarity functions using a first loss function based on an output of application of the approximation function to the first context training data, wherein the first context weights are stored for use as part of the first context-specific composite similarity function;
receiving a query entity;
applying the trained first context-specific composite similarity function to the query entity to determine a similarity measure between an entity feature vector of the query entity and each of a plurality of candidate entity feature vectors, wherein each candidate entity feature vector represents a candidate entity;
selecting, based on the determined similarity measures, two or more of the candidate entity feature vectors;
ranking, based on the determined similarity measures, two or more candidate entities represented by the two or more selected candidate entity feature vectors, wherein the candidate entities are ranked with the similarity measure that represents a closest similarity between the query entity and the candidate entity;
displaying, on a user interface, a ranked list of the two or more ranked candidate entities; and
determining, by a clinician decision application, based on the ranked list of the two or more ranked candidate entities, a decision regarding the query entity.

2. The method of claim 1 further comprising:
providing a second plurality of labeled entity vectors as second context training data;
applying the approximation function to approximate, for each respective labeled entity vector of the second context training data, a second context label for the respective labeled entity vector data based on an output of the composite similarity function and respective second context labels of the other labeled entity vectors of the second context training data; and
training a second context specific composite similarity function based on the composite similarity function, wherein training the second context specific composite similarity function includes learning second context weights for the plurality of template similarity functions using a second loss function based on an output of application of the approximation function to the second context training data, wherein the second context weights are stored for use as part of the second context-specific composite similarity function.

3. The method of claim 2, wherein the first context-specific composite similarity function is applicable to a subsequent query entity feature vector and a subsequent candidate entity feature vector to determine a similarity measure between the subsequent query entity feature vector and the subsequent candidate entity feature vector in a first medical context; and wherein the second context-specific composite similarity function is applicable to the subsequent query entity feature vector and the subsequent candidate entity feature vector to determine another similarity measure between the subsequent query entity feature vector and the subsequent candidate entity feature vector in a second medical context that is different than the first medical context.

4. The method of claim 3, wherein the first medical context comprises hemodynamic stability.

5. The method of claim 4, wherein the second medical context comprises acute kidney injury.

6. The method of claim 1, wherein providing the plurality of template similarity functions comprises:

selecting at least one feature shared by the query entity feature vector and the candidate entity feature vector;

determining a population distribution for the selected feature across a plurality of candidate entities;

providing a given template similarity function of the plurality of template similarity functions, wherein the given template similarity function computes a cumulative probability score of any entity having a selected feature value between a selected feature value of the query entity feature vector and a selected feature value of the candidate entity feature vector according to the determined population distribution.

7. The method of claim 6, wherein the given template similarity function is further normalized based on an average similarity score of at least one of the query entity feature vector and the candidate entity feature vector to other entities across the determined population distribution.

8. The method of claim 1, wherein the approximation function comprises a kernel-smoothing function.

9. A system comprising one or more processors and memory operably coupled with the one or more processors, wherein the memory stores instructions that, in response to execution of the instructions by one or more processors, cause the one or more processors to perform the following operations:

providing a plurality of template similarity functions, wherein each template similarity function of the plurality of template similarity functions compares a respective subset of features of a query entity feature vector with a corresponding subset of features of a candidate entity feature vector;

providing a composite similarity function as a weighted combination of respective outputs of the plurality of template similarity functions;

providing a first plurality of labeled entity vectors as first context training data;

applying an approximation function to approximate, for each respective labeled entity vector of the first context training data, a first context label for the respective labeled entity vector data based on an output of the composite similarity function and respective first context labels of the other labeled entity vectors of the first context training data;

training a first context specific composite similarity function based on the composite similarity function, wherein training the first context specific composite similarity function includes learning first context weights for the plurality of template similarity functions using a first loss function based on an output of application of the approximation function to the first context training data, wherein the first context weights are stored for use as part of the first context-specific composite similarity function;

receiving a query entity;

applying the trained first context-specific composite similarity function to the query entity to determine a similarity measure between an entity feature vector of the query entity and each of a plurality of candidate entity feature vectors, wherein each candidate entity feature vector represents a candidate entity;

selecting, based on the determined similarity measures, two or more of the candidate entity feature vectors;

ranking, based on the determined similarity measures, two or more candidate entities represented by the two or more selected candidate entity feature vectors, wherein the candidate entities are ranked with the similarity measure that represents a closest similarity between the query entity and the candidate entity;

displaying, on a user interface, a ranked list of the two or more ranked candidate entities; and determining, by a clinician decision application, based on the ranked list of the two or more ranked candidate entities, a decision regarding the query entity.

10. The system of claim 9 further comprising instructions to perform the following operations:

providing a second plurality of labeled entity vectors as second context training data;

applying the approximation function to approximate, for each respective labeled entity vector of the second context training data, a second context label for the respective labeled entity vector data based on an output of the composite similarity function and respective second context labels of the other labeled entity vectors of the second context training data; and training a second context specific composite similarity function based on the composite similarity function, wherein training the second context specific composite similarity function includes learning second context weights for the plurality of template similarity functions using a second loss function based on an output of application of the approximation function to the second context training data, wherein the second context weights are stored for use as part of the second context-specific composite similarity function.

11. The system of claim 10, wherein the first context-specific composite similarity function is applicable to a subsequent query entity feature vector and a subsequent candidate entity feature vector to determine a similarity measure between the subsequent query entity feature vector and the subsequent candidate entity feature vector in a first medical context; and wherein the second context-specific composite similarity function is applicable to the subsequent query entity feature vector and the subsequent candidate entity feature vector to determine another similarity measure between the subsequent query entity feature vector and the subsequent candidate entity feature vector in a second medical context that is different than the first medical context.

12. The system of claim 11, wherein the first medical context comprises hemodynamic stability.

13. The system of claim 12, wherein the second medical context comprises acute kidney injury.

14. The system of claim 9, wherein providing the plurality of template similarity functions comprises:

selecting at least one feature shared by the query entity feature vector and the candidate entity feature vector;

determining a population distribution for the selected feature across a plurality of candidate entities;

providing a given template similarity function of the plurality of template similarity functions, wherein the given template similarity function computes a cumulative probability score of any entity having a selected feature value between a selected feature value of the query entity feature vector and a selected feature value of the candidate entity feature vector according to the determined population distribution.

15. The system of claim 14, wherein the given template similarity function is further normalized based on an average similarity score of at least one of the query entity feature vector and the candidate entity feature vector to other entities across the determined population distribution.

16. The system of claim 9, wherein the approximation function comprises a kernel-smoothing function.

17. At least one non-transitory computer-readable medium comprising instructions that, in response to execution of the instructions by one or more processors, cause the one or more processors to perform the following operations:

providing a plurality of template similarity functions, wherein each template similarity function of the plurality of template similarity functions compares a respective subset of features of a query entity feature vector with a corresponding subset of features of a candidate entity feature vector;

providing a composite similarity function as a weighted combination of respective outputs of the plurality of template similarity functions;

providing a first plurality of labeled entity vectors as first context training data;

applying an approximation function to approximate, for each respective labeled entity vector of the first context training data, a first context label for the respective labeled entity vector data based on an output of the composite similarity function and respective first context labels of the other labeled entity vectors of the first context training data;

training a first context specific composite similarity function based on the composite similarity function, wherein training the first context specific composite similarity function includes learning first context weights for the plurality of template similarity functions using a first loss function based on an output of application of the approximation function to the first context training data, wherein the first context weights are stored for use as part of the first context-specific composite similarity function;

receiving a query entity;

applying the trained first context-specific composite similarity function to the query entity to determine a similarity measure between an entity feature vector of the query entity and each of a plurality of candidate entity feature vectors, wherein each candidate entity feature vector represents a candidate entity;

selecting, based on the determined similarity measures, two or more of the candidate entity feature vectors;

ranking, based on the determined similarity measures, two or more candidate entities represented by the two or more selected candidate entity feature vectors, wherein the candidate entities are ranked with the similarity measure that represents a closest similarity between the query entity and the candidate entity;

displaying, on a user interface, a ranked list of the two or more ranked candidate entities; and determining, by a clinician decision application, based on the ranked list of the two or more ranked candidate entities, a decision regarding the query entity.

18. The at least one non-transitory computer-readable medium of claim 17, further comprising instructions to perform the following operations:

providing a second plurality of labeled entity vectors as second context training data;

applying the approximation function to approximate, for each respective labeled entity vector of the second context training data, a second context label for the respective labeled entity vector data based on an output of the composite similarity function and respective second context labels of the other labeled entity vectors of the second context training data; and training a second context specific composite similarity function based on the composite similarity function, wherein training the second context specific composite similarity function includes learning second context weights for the plurality of template similarity functions using a second loss function based on an output of application of the approximation function to the second context training data, wherein the second context weights are stored for use as part of the second context-specific composite similarity function.

19. The at least one non-transitory computer-readable medium of claim 18, wherein the first context-specific composite similarity function is applicable to a subsequent query entity feature vector and a subsequent candidate entity feature vector to determine a similarity measure between the subsequent query entity feature vector and the subsequent candidate entity feature vector in a first medical context; and wherein the second context-specific composite similarity function is applicable to the subsequent query entity feature vector and the subsequent candidate entity feature vector to determine another similarity measure between the subsequent query entity feature vector and the subsequent candidate entity feature vector in a second medical context that is different than the first medical context.

20. The at least one non-transitory computer-readable medium of claim 19, wherein the first medical context comprises hemodynamic stability.

* * * * *